United States Patent
Lee (10) Patent No.: US 6,899,725 B2
(45) Date of Patent: May 31, 2005

(54) BED FOR DIAGNOSIS HAVING FUNCTIONS OF BLOCKING WATER VEIN AND ELECTROMAGNETIC WAVE AND GENERATING ULTRA-LONG WAVE

(76) Inventor: Kyung-bok Lee, 101-510 Hosu-Imkwang Apt., Songpa 1-dong, Songpa-gu, Seoul (KR)

( * ) Notice: Subject to any disclaimer, the term of this patent is extended or adjusted under 35 U.S.C. 154(b) by 144 days.

(21) Appl. No.: 10/455,809

(22) Filed: Jun. 6, 2003

(65) Prior Publication Data

US 2004/0177448 A1 Sep. 16, 2004

(30) Foreign Application Priority Data

| Mar. 10, 2003 | (KR) | 10-2003-0014765 |
| Mar. 10, 2003 | (KR) | 10-2003-0014766 |
| Mar. 10, 2003 | (KR) | 10-2003-0014763 |
| Mar. 10, 2003 | (KR) | 10-2003-0014761 |
| Mar. 10, 2003 | (KR) | 10-2003-0014760 |
| Mar. 10, 2003 | (KR) | 10-2003-0014764 |

(51) Int. Cl.$^7$ .................................................. A61N 5/06
(52) U.S. Cl. .......................... 607/96; 5/690; 607/98; 607/100
(58) Field of Search ..................... 5/590; 607/96–103

(56) References Cited

U.S. PATENT DOCUMENTS 6,108,581 A * 8/2000 Jung .......................... 607/100

FOREIGN PATENT DOCUMENTS

| EP | 963138 A2 * 12/1999 | H05B/3/34 |
| KR | 2001025796 A * 4/2001 | A61N/5/06 |

* cited by examiner

*Primary Examiner*—Roy D Gibson
*Assistant Examiner*—Henry M Johnson, III
(74) *Attorney, Agent, or Firm*—Shlesinger, Arkwright & Garvey LLP (57) ABSTRACT

Disclosed is a bed for diagnosis which can block a water vein and an electromagnetic wave and generate an ultra-long wave. The bed prevents the influence of a water vein or an electromagnetic wave on a patient or a sleeper, and alleviates pains on various parts of the body by its function of thermotheraphy. In addition, the bed generates far-infrared and ultra-long waves to expedite the recovery of health. The bed comprises a plurality of supporting legs 102 each having a wheel 101 for horizontal movement at the lower end thereof; at least one height adjusting plate 103 at the upper part of said supporting legs 102; a metal frame 104 surrounding said height adjusting plate 103 and fixed at the upper part of said supporting legs 102; an upper plate 110 mounted over said height adjusting plate 103 and said metal frame 104 and consisting, from the bottom, of an outer cover 111, an outer frame 112, a water vein blocking alumina 113, a dampproof paper 114, urethane 115, an insulating sheet 116, a calescent carbon heater 117, an insulating sheet 118, an ultra-long wave generating section 130, a copper wire 119 for blocking a water vein, a copper plate 120 for blocking a water vein and an electromagnetic wave, a biogene 121 and a hardened layer 122; and an electromagnetic wave absorbing section 140 connected to said copper plate 120 of said upper plate 110 by a conductive wire for absorbing and eliminating electromagnetic waves.

8 Claims, 11 Drawing Sheets

BED FOR DIAGNOSIS HAVING FUNCTIONS OF BLOCKING WATER VEIN AND ELECTROMAGNETIC WAVE AND GENERATING ULTRA-LONG WAVE

FIELD OF THE INVENTION

The present invention relates to a bed for diagnosis having functions of blocking a water vein and an electromagnetic wave and generating an ultra-long wave, and more particularly to a bed for diagnosis which can block a water vein and an electromagnetic wave and generate an ultra-long wave, and which can prevent the influence of a water vein or an electromagnetic wave on a patient or a sleeper, alleviate pains on various parts of the body by its function of thermotherapy and generate far-infrared and ultra-long waves to expedite the recovery of health.

BACKGROUND OF THE INVENTION

Figure 1:
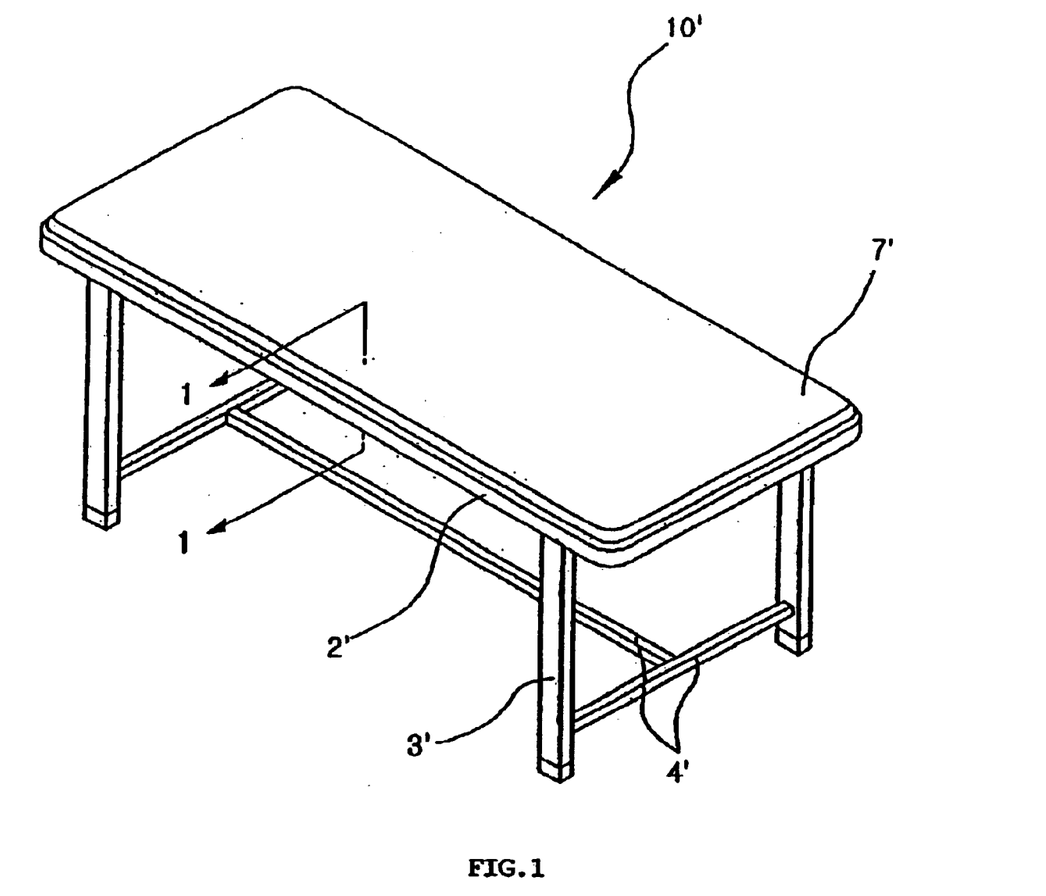
FIG. 1 is a perspective view of a conventional bed for diagnosis.
Figure 2:
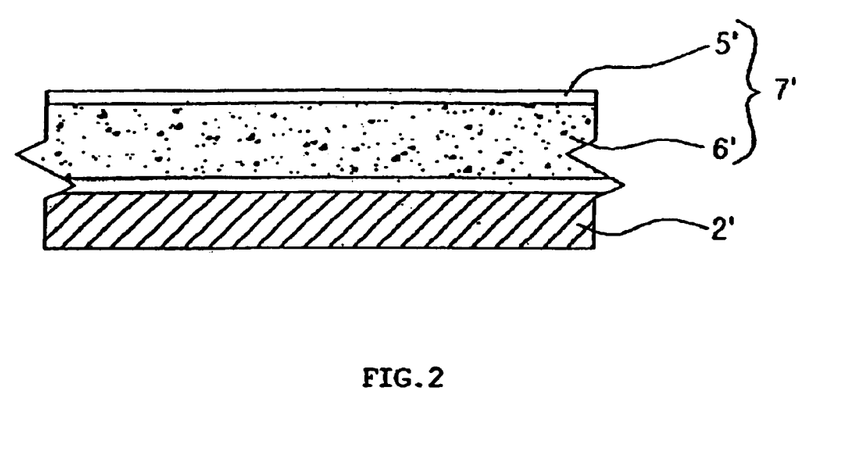
FIG. 2 is an enlarged, cross-sectional view, of a conventional bed taken along line 1—1 of FIG. 1.

FIG. 1 is a perspective view of a conventional bed 10' for diagnosis. FIG. 2 is an enlarged, cross-sectional view of a conventional bed taken along line 1—1 of FIG. 1.

As shown in FIGS. 1 and 2, the conventional bed 10' for diagnosis comprises a substantially rectangular metal plate 2', a plurality of supporting legs 3' which extend downward at a particular distance from four corners of the metal plate 2' to fix the metal plate 2' at a particular height, connection members, 4' for fixing and connecting the supporting legs 3' with each another, and an upper plate 7' mounted over the metal plate 2' and consisting of a sponge 6' and an outer cover 5' such that a patient can sit or lie down.

It is known that groundwater flowing below the ground generates water veins having complicated waveforms. Water veins adversely influence humans and particularly patients, because various minerals dissolved in the groundwater gather into the water veins to cause changes in a magnetic charge. In other words, water veins cause changes in terrestrial magnetic force and electric current, thereby influencing, life on the earth. Water vein with great destructibility may damage buildings and precise machinery, as well as humans and animals. It is also known that water veins influence even the top floor of a skyscraper. Particularly, living things are greatly influenced by water veins while sleeping, although hardly influenced while moving.

As stated above, a conventional bed for diagnosis comprises an upper plate simply having a sponge and an outer cover over a metal plate. The conventional bed lets a patient exposed to the hazardous environment of water veins.

If there is a water vein under the conventional bed, the patient on the bed will directly receive an adverse impact from the water vein. As a result, there may be such problems that recovery from pain will be delayed, drugs will be ineffective, or pains will become more serious.

Moreover, the conventional bed cannot produce a thermotherapy effect which is an optimum treatment condition for patients. The conventional bed does not have various functions for improving health.

Electric mats may have been used to give a thermotherapy effect to the patient laying on the conventional bed. However, electric mats generate large amounts of electromagnetic waves that cause lassitude, insomnia, nervousness, headache, bad sleep, or the like.

Electromagnetic waves may also cause leukemia, lymphoma, brain cancer, central nervous system cancer, breast cancer, dementia, abortion and delivery of a malformed child. Electromagnetic waves are known to be particularly hazardous to pregnant women.

In addition, the conventional bed for diagnosis does not have a function of generating far-infrared and ultra-long waves which are helpful in the recovery of health.

OBJECTS AND SUMMARY OF THE INVENTION

Accordingly, the present invention has been made to solve the above-mentioned problems occurring in the prior art, and an object of the present invention is to provide a bed for diagnosis which can block a water vein and an electromagnetic wave and generate an ultra-long wave, and which can prevent the influence of a water vein or an electromagnetic wave on a patient or a sleeper, alleviate pains on various parts of the body by its function of thermotheraphy and generate far-infrared and ultra-long waves to expedite the recovery of health.

In order to accomplish this object, there is provided a bed for diagnosis comprising a plurality of supporting legs each having a wheel for horizontal movement at the lower end thereof; at least one height adjusting plate at the upper part of said supporting legs; a metal frame surrounding said height adjusting plate and fixed at the upper part of said supporting legs; an upper plate mounted over said height adjusting plate and said metal frame and consisting, from the bottom, of an outer cover, an outer frame, a water vein blocking alumina, a dampproof paper, urethane, an insulating sheet, a calescent carbon heater, an insulating sheet, an ultra-long wave generating section, a copper wire for blocking a water vein, a copper plate for blocking a water vein and an electromagnetic wave, a biogene and a hardened layer; and an electromagnetic wave absorbing section connected to said copper plate of said upper plate by a conductive wire for absorbing and eliminating electromagnetic waves.

The hardened layer of the upper plate may comprise a stone selected from granite, emerald, yellow jade, corundum, blue elvan and yellow elvan which contain a large amount of germanium.

In addition, the hardened layer of the upper plate may be an ocher layer formed by mixing 60% by weight of reddish brown clay, 15% by weight of silicon dioxide, 10% by weight of mineral powder (biotite), 7% by weight of a thickener, 3% by weight of pulp and 5% by weight of anhydrite, and extrusion molding the mixture.

A control section for supplying power is provided on the outer frame of the upper plate. A carton heater can be connected to the control section.

One end of the electromagnetic wave absorbing section, which has a resistance R, a condenser C and an inductor L in parallel connection to a power line, can be connected by a conductive wire to the copper plate for blocking a water vein and an electromagnetic wave.

The ultra-long wave generating section comprises substantially bar-type permanent magnets and a plurality of ultra-long wave coils winding around the permanent bar magnets. An alternating current can be supplied to the ultra-long wave coils from the control section.

In addition, a height adjuster for controlling the height adjusting plate is provided on the outer periphery of the metal frame. The height adjuster controls the height of at least one height adjusting plate, thereby changing the slope of the upper plate.

In order to accomplish the object of the present invention, there is also provided a bed for diagnosis having functions of blocking a water vein and an electromagnetic wave and generating an ultra-long wave, and comprising a plurality of supporting legs having the same plane; a bedplate mounted on the supporting legs and having a shape of hexahedron with an open top; an upper plate mounted over said bedplate and consisting, from the bottom, of an outer cover, an outer frame, a water vein blocking alumina, a dampproof paper, urethane, an insulating sheet, a calescent carbon heater, an insulating sheet, an ultra-long wave generating section, a copper wire for blocking a water vein, a copper plate for blocking a water vein and an electromagnetic wave, a biogene and a hardened layer; and an electromagnetic wave absorbing section connected to said copper plate of said upper plate by a conductive wire for absorbing and eliminating electromagnetic waves.

According to the second embodiment of the present invention mentioned above, the bed for diagnosis can prevent the influence of a water vein from the underground by the alumina, copper wire and copper plate included in the upper plate.

Further, the carbon heater offers a thermotherapy effect to a patient laying on the bed to alleviate pains on the body and help effective working of drugs.

The electromagnetic wave absorbing section absorbs and eliminates electromagnetic waves, which may be generated from the carbon heater or the like, so as to prevent the patient from being exposed to the electromagnetic waves.

The ultra-long wave generating section generates ultra-long waves that directly work on the patient laying on the bed, thereby rapidly alleviating pains on the body and providing an environment advantageous to the health.

Also, the bed for diagnosis according to the present invention includes a biogene, as well as a stone layer or an ocher layer as the hardened layer, in order to emit large amounts of far-infrared rays.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, preferred embodiments of the present invention will be described with reference to the accompanying drawings. In the following description and drawings, the same reference numerals are used to designate the same or similar components, and so repetition of the description on the same or similar components will be omitted.

Figure 3:
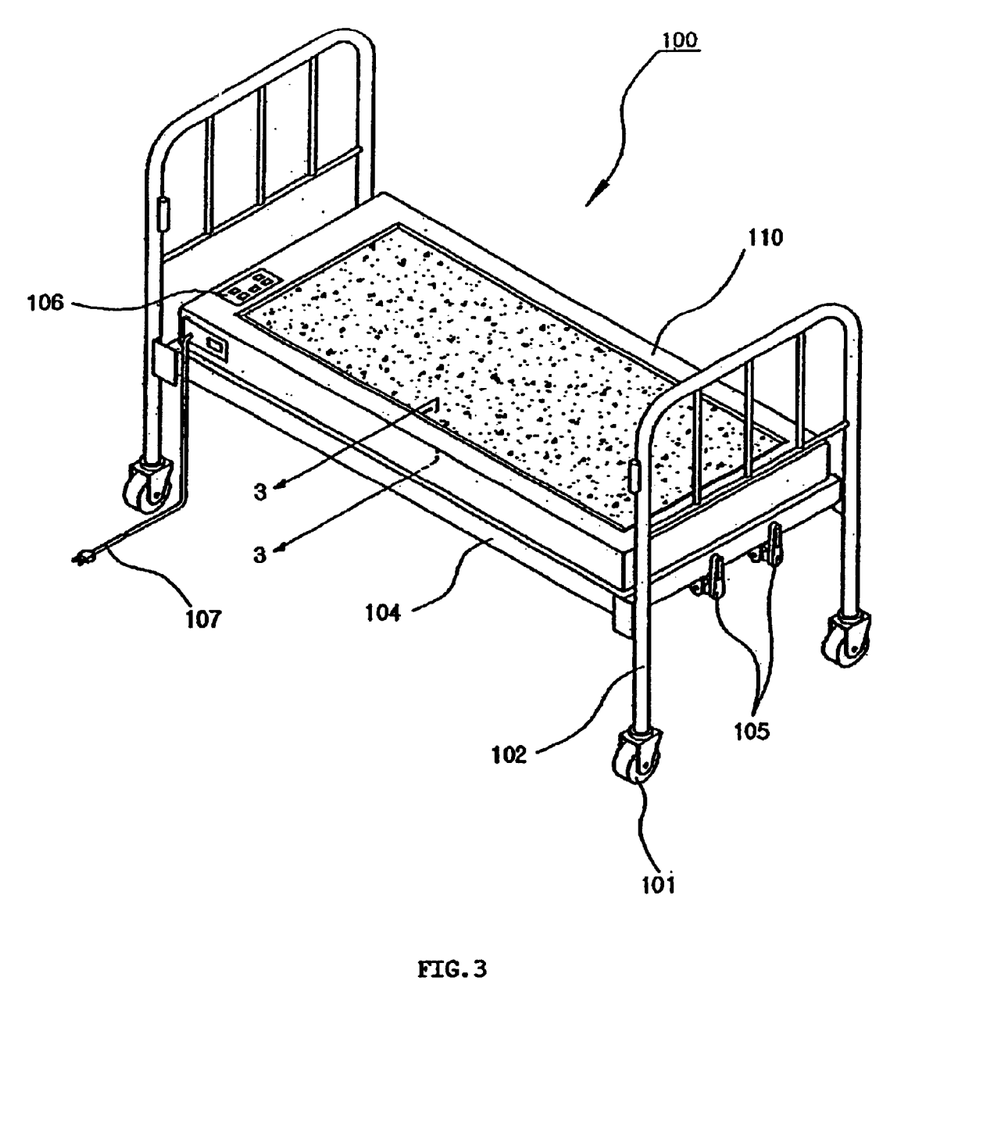
FIG. 3 is a perspective view showing a bed for diagnosis having functions of blocking a water vein and an electromagnetic wave and generating an ultra-long wave according to one embodiment of the present invention.
Figure 4:
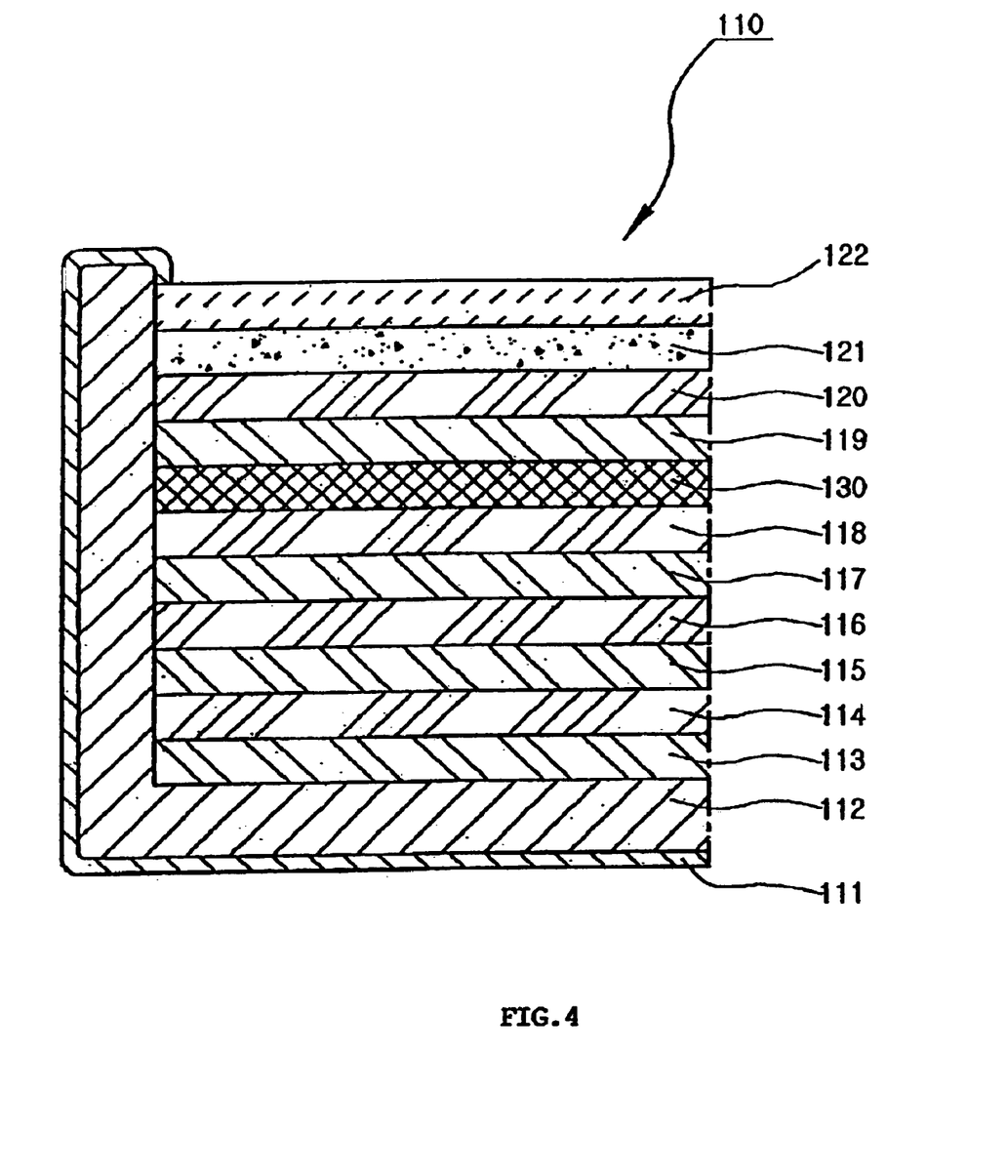
FIG. 4 is an enlarged, cross-sectional view taken along line 3—3 of FIG. 3.

FIG. 3 is a perspective view of a bed 100 for diagnosis having functions of blocking a water vein and an electromagnetic wave and generating an ultra-long wave according to one embodiment of the present invention. FIG. 4 is an enlarged, cross-sectional view taken along line 3—3 of FIG. 3.

As shown in the drawings, the bed 100 comprises a plurality of supporting legs 102, a metal frame 104 positioned at the upper part of the supporting legs 102, an upper plate 110 mounted over the metal frame 104 and an electromagnetic wave absorbing section 140 connected to the upper plate 110 for blocking electromagnetic waves.

Each supporting leg 102 has, a wheel 101 for horizontal movement at the lower end thereof. The wheel 101 is in substantially "∩" shape.

The metal frame 104 is provided at the upper part of the supporting legs 102, and contains at least one height adjusting plate 103 (see FIGS. 8 and 9) in the inside thereof. A height adjuster 105 for easily controlling the height of the height adjusting plate 103 is provided on one side of the metal frame 104. Since the mechanical connection of the height adjusting plate 103 with the height adjuster 105 has a structure commonly adopted in a bed for diagnosis, a detailed explanation of the connection will be omitted.

The upper plate 110 is mounted over the height adjusting plate 103 and the metal frame 104. The upper plate 110 consists from the bottom, of an outer cover 111 made of a natural or synthetic leather, an outer frame 112 made of wood to exhibit superior heat insulation, a water vein blocking alumina 113, a dampproof paper 114, urethane 115 with superior heat insulation, an insulating sheet 116 for blocking a leakage current, a calescent carbon heater 117, an insulating sheet 118 for blocking a leakage current, a copper wire 119 for blocking a water vein, a copper plate 120 for blocking a water vein and an electromagnetic wave, a biogene 121 for generating far-infrared rays and a hardened layer 122.

The outer frame 112 is in the shape of a hexahedron with an open top, and is enveloped by the outer cover 111. The other elements are laid in regular sequence to form the upper plate 110.

The biogene 121 is obtained by heating various clays at a temperature of 1,200 to 1,700° C.

The hardened layer 122 may comprise a stone selected from granite, emerald, yellow jade, corundum, blue elvan and yellow elvan which contain a large amount of germanium. In addition, the hardened layer 122 may be an ocher layer formed by mixing 60% by weight of reddish brown clay, 15% by weight of silicon dioxide, 10% by weight of mineral powder (biotite), 7% by weight of a thickener, 3% by weight of pulp and 5% by weight of anhydrite, and extrusion molding the mixture.

The hardened layer 122 comprising a stone or an ocher emits far-infrared rays having a wavelength of 8 to 11 $\mu$m, which is the most advantageous to the human body among infrared rays. The far-infrared rays permeate into the deep skin (into the depth of 4 to 5 cm) to make cells resonate and thereby to increase the body temperature. With the increase of the temperature, the capillary vessels are expanded and the blood circulation is activated to accelerate metabolism. Also, the increase of the regeneration rate greatly promotes the growth. Particularly, due to the heavy perspiration effect obtained by perspiring a lot, various noxious substances, waste products, heavy metals and so on are eliminated from the body so that the acidified body can be changed to have an alkaline constitution. Also, the heavy perspiration relaxes both the body and the mind to deal with stress which can be a cause of adult diseases.

The upper plate 110 has, on one end thereof, a control section 106 for supplying power to the carbon heater 117 and the ultra-long wave generating section 130 and for absorbing and eliminating electromagnetic waves. An electric code 107, for supplying power to the upper plate 110 is connected to one side of the upper plate 110.

Figure 5:
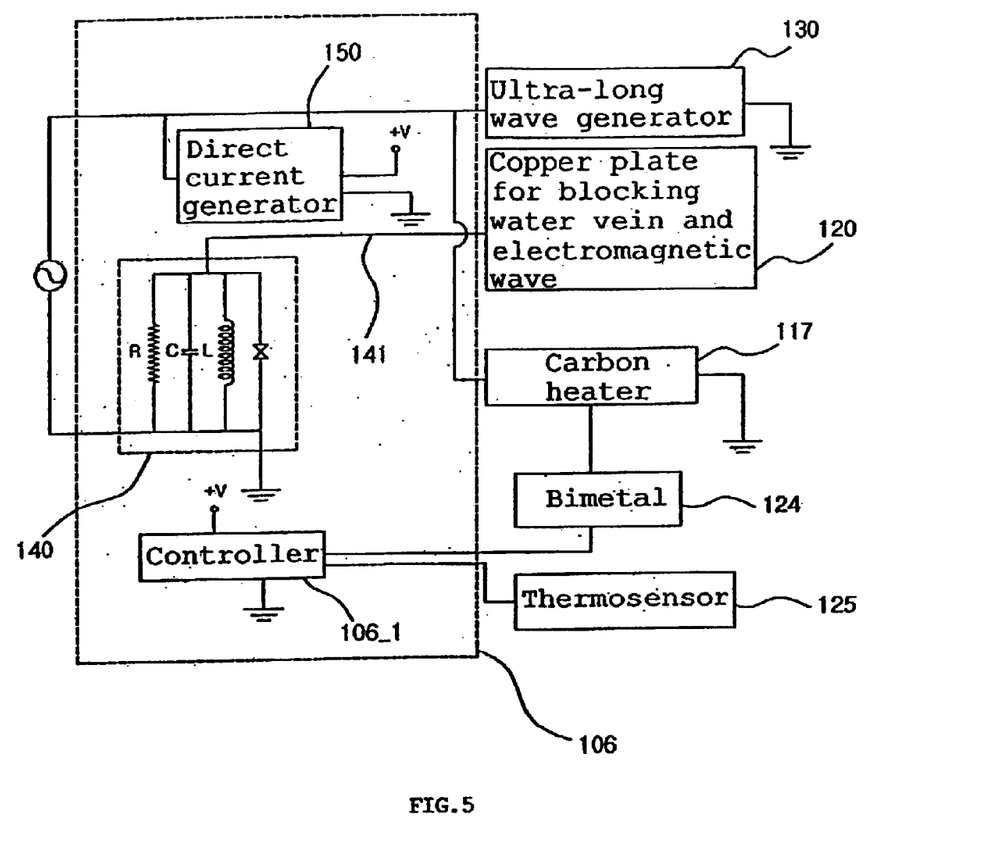
FIG. 5 is a circuit diagram showing the electrical constructions, such as an electromagnetic wave absorbing section, an ultra-long wave generating section and a carbon heater, in a bed for diagnosis having functions of blocking a water vein and an electromagnetic wave and generating an ultra-long wave according to the present invention.

FIG. 5 illustrates the electrical constructions, such as the electromagnetic wave absorbing section 140, the ultra-long wave generating section 130 and the carbon heater 117, in the bed 100 for diagnosis having functions of blocking a water vein and an electromagnetic wave according to the present invention.

Figure 6:
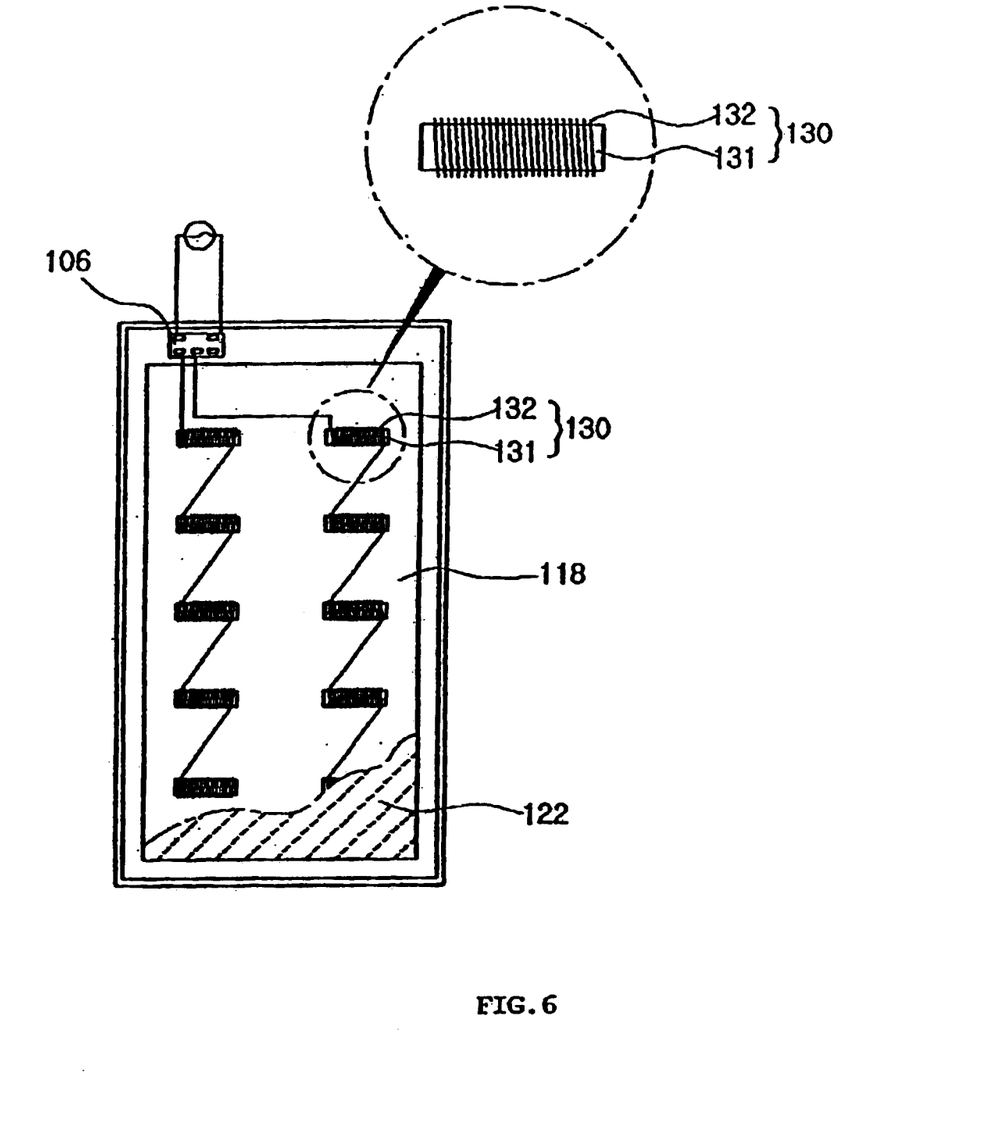
FIG. 6 is a plan showing in detail an ultra-long wave generating section in a bed for diagnosis having functions of blocking a water vein and an electromagnetic wave and generating an ultra-long wave, according to the present invention.

FIG. 6 illustrates in detail the ultra-long wave generating section 130 in the bed 100 for diagnosis having functions of blocking a water vein and an electromagnetic wave and generating an ultra-long wave according to the present invention.

Figure 7:
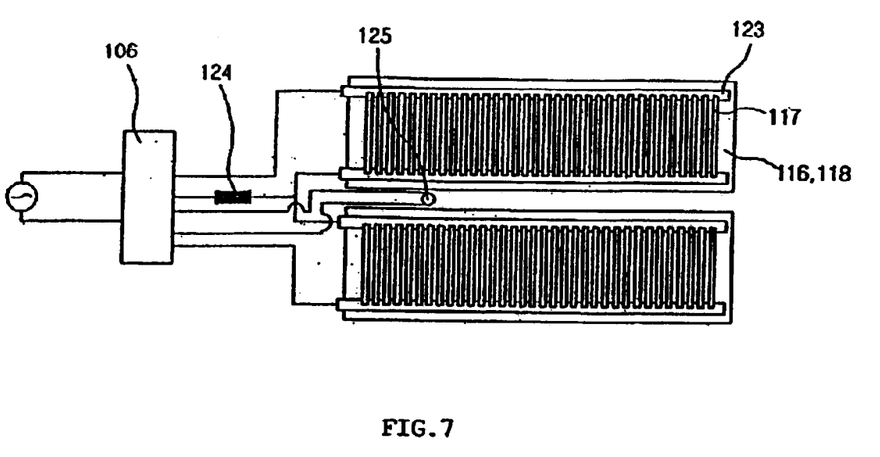
FIG. 7 is a plan showing in detail a carbon heater and surrounding structures in a bed for diagnosis having functions of blocking a water vein and an electromagnetic wave and generating an ultra-long wave according to the present invention.

FIG. 7 illustrates in detail the carbon heater 117 and surrounding structures in the bed 100 for diagnosis having functions of blocking a water vein and an electromagnetic wave and generating an ultra-long wave according to the present invention.

The electromagnetic wave absorbing section 140 is connected by a conductive wire 141 to the copper plate 120 for blocking a water vein and an electromagnetic wave, which is mounted over the copper wire 119 of the upper plate 110. The conductive wire 141 is connected to a resistance R, a condenser C and an inductor L in parallel connection. Of course, one end of each of resistance R, condenser C and inductor L is connected to an AC power, while the other end is grounded. Thus, electromagnetic waves generated from the carbon heater 117 or the like are delivered to the electromagnetic wave absorbing section 140 through the copper plate 120 and the conductive wire 141, and absorbed or eliminated by the condenser C or ground of the electromagnetic wave absorbing section 140. Although only the structure of connecting the electromagnetic wave absorbing section 140 to the copper plate 120 by the conductive wire 141 is described herein, it is also possible to connect the electromagnetic wave absorbing section 140 to the copper wire 119 and/or the water vein blocking alumina 113 by the conductive wire 141. The structure is not to be limited by the above description.

The ultra-long wave generating section 130 is connected to the AC power through the control section 106.

As shown in FIG. 6, a plurality of permanent magnets 131 are disposed on the insulating sheet 118 of the upper plate 110 and wound around by ultra-long wave coils 132. Each ultra-long wave coil 132 is connected in series to the control section 106 which is connected to the AC power. The ultra-long wave generating section 130, being connected to the AC power through the control section 106, can generate ultra-long waves having a predetermined wavelength.

The ultra-long wave generating section 130 maybe termed an alternating magnetic field generator, because the strength of the magnetic field changes with time in particular cycles. When an AC power with a lowered current is inputted into the control section 106, the N and S poles change to each other at a speed of 50 to 60 times per second in the ultra-long wave generating section 130 to generate ultra-long waves. The ultra-long waves penetrate into all materials including glass, wood, fiber, stone and rubber, and work on the nerves in the bone marrow in the depth of human body. The ultra-long waves serve magnetization of carbon, oxygen, nitrogen, manganese and iron in human tissues and stimulate cells to improve the cell regeneration.

The carbon heater 117 is connected to the AC power through the control section 106. More specifically, the carbon heater 117 is connected to a controller 106_1 through a bimetal 124. Also, a thermosensor 125 is connected to the controller 106_1 to prevent the overheating of the carbon heater 117.

As illustrated in FIG. 7, the carbon heater 117 is directly connected to the control section 106. More specifically, the carbon heater 117 has a plurality of heat coils disposed at equal intervals. A copper pattern 123 is connected to each end of the carbon heater 117. When power is supplied to the copper pattern 123, the carbon heater 117 will generate a constant Joule heat. In order to prevent a leakage current, insulating sheets 116 and 118 are respectively placed under and over the carbon heater 117 and the copper pattern 123. In addition, the bimetal 124 is connected to the control section 106 to prevent overheating, and the thermosensor 125 is provided to monitor the temperature of the upper plate 110. The thermosensor 125 can be a conventional thermistor or an equivalent thereof and is not to be limited to a particular type.

Also, a direct current generator 150 (which is provided within the control section 106) is connected to the AC power. The direct current power generated by the direct current generator 150 is supplied to the controller 106_1 (see FIG. 5).

Figure 8:
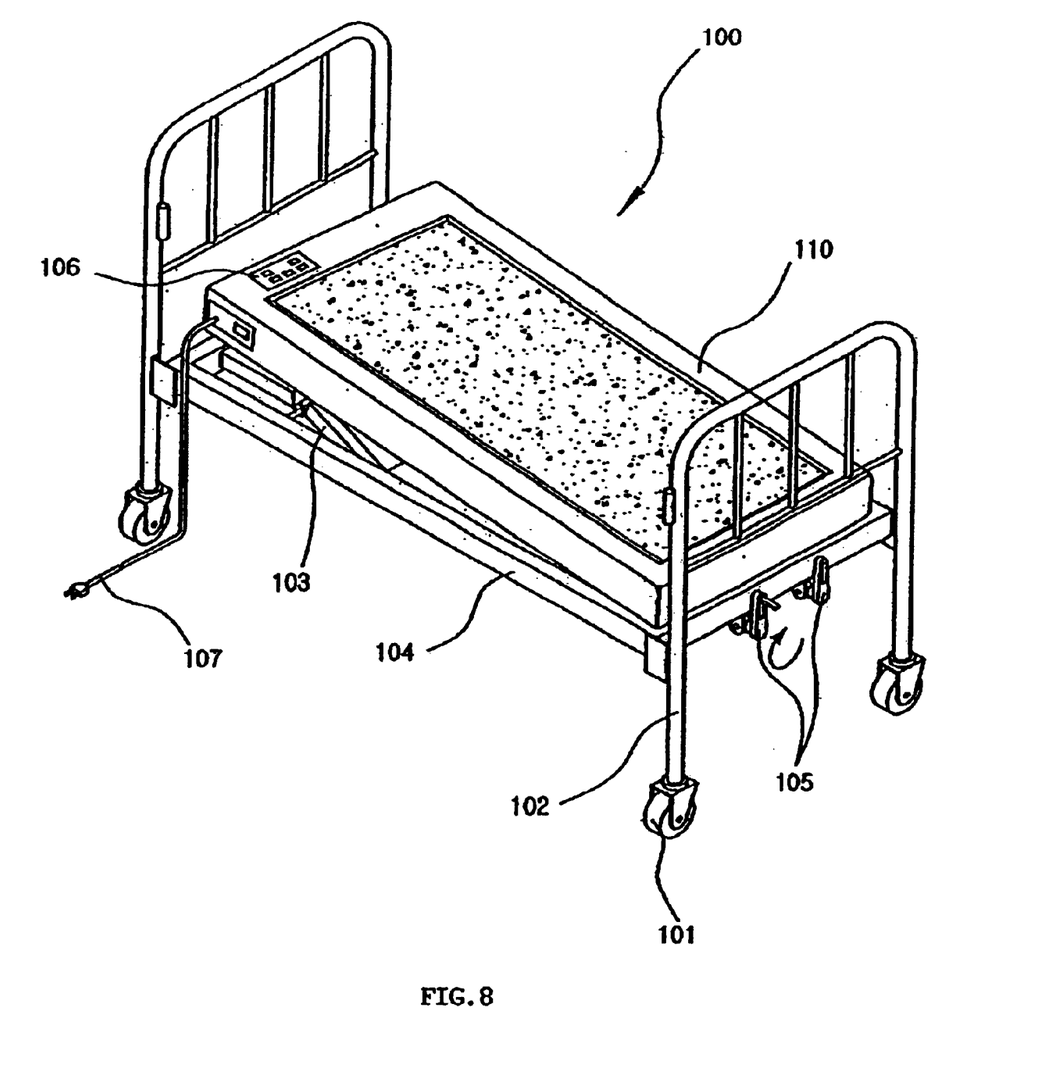
FIG. 8 is a perspective view showing the lifted-up state of an upper plate, of a bed for diagnosis having functions of blocking a water vein and an electromagnetic wave and generating an ultra-long wave according to the present invention.
Figure 9:
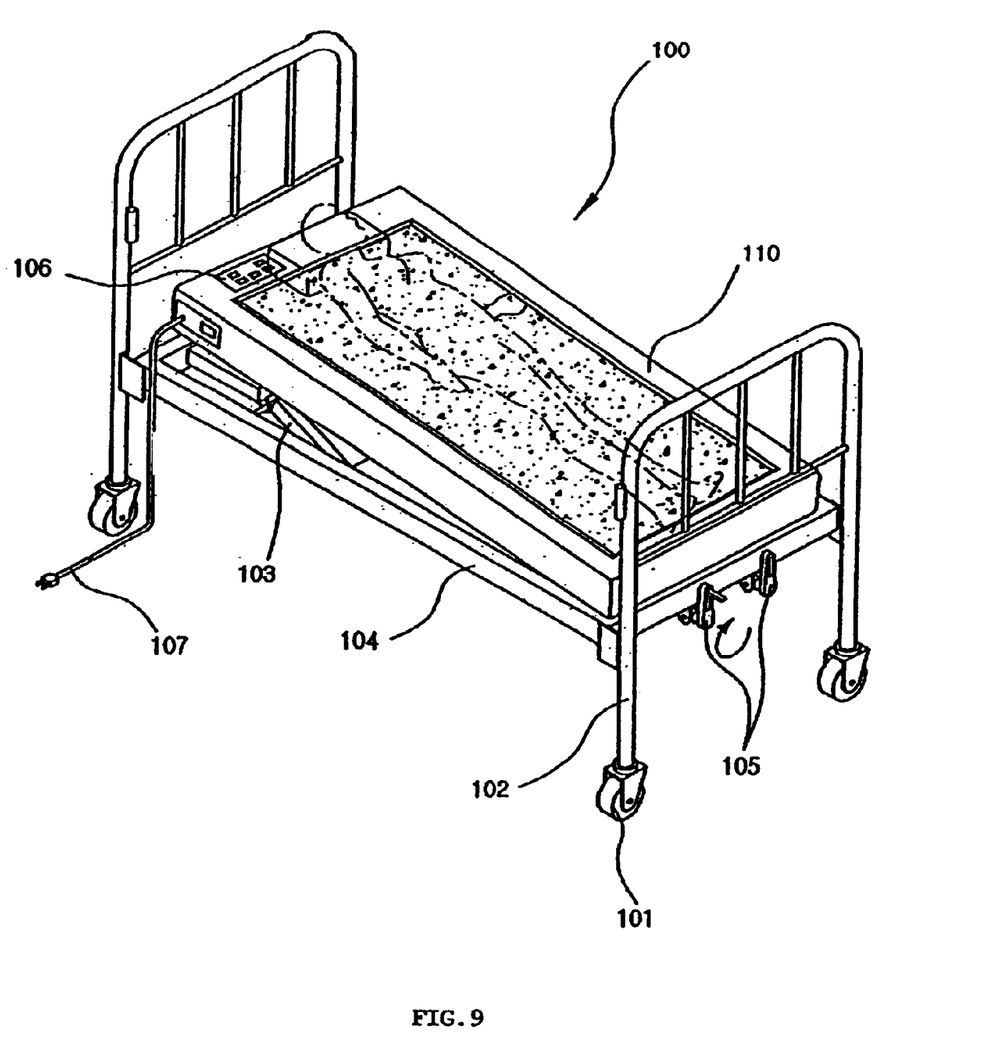
FIG. 9 is a perspective view showing the use of a bed for diagnosis having functions of blocking a water vein and an electromagnetic wave and generating an ultra-long wave according to the present invention.

FIG. 8 shows the lifted-up state of the upper plate 110 of the bed 100 for diagnosis having functions of blocking a water vein and an electromagnetic wave and generating an ultra-long wave according to the present invention. FIG. 9 shows the use of the bed 100 for diagnosis having functions of blocking a water vein and an electromagnetic wave and generating an ultra-long wave according to the present invention.

As shown in FIGS. 8 and 9, by turning the height adjuster 105 which is fixed on one side of the metal frame 104, it is possible to adjust the height of the height adjusting plate 103 within the metal frame 104 and change the slope of the upper plate 110 mounted over the height adjusting plate 103 and the metal frame 104 so that a patient can lie on the bed in the most comfortable condition.

In the bed 100 for diagnosis having functions of blocking a water vein and an electromagnetic wave and generating an ultra-long wave, layers of the alumina 113, copper wire 119 and copper plate 120 forming the upper plate 110 prevent the adverse influence of underground water veins on the patient laying on the upper plate 110.

Also, the electromagnetic wave absorbing section 140 is connected to the alumina 123, the copper wire 119 and/or the copper plate 120 through the conductive wire 141 in order to absorb or eliminate electromagnetic waves generated from the carbon heater 117 or the like and to shield the patient from hazardous electromagnetic waves.

In the bed 100 for diagnosis having functions of blocking a water vein and an electromagnetic wave and generating an ultra-long wave, the carbon heater 117 connected to the control section 106 generates heat. Consequently, the biogene 121 and the hardened layer 122 generate large amounts of far-infrared rays and heat the upper plate 110 to a suitable temperature to provide the optimum condition to a patient or a sleeper.

The ultra-long wave generating section 130 in the bed 100 for diagnosis generates ultra-long waves that directly work on the patient laying on the bed, thereby promoting the circulation of blood and reducing the period of recovery.

Figure 10:
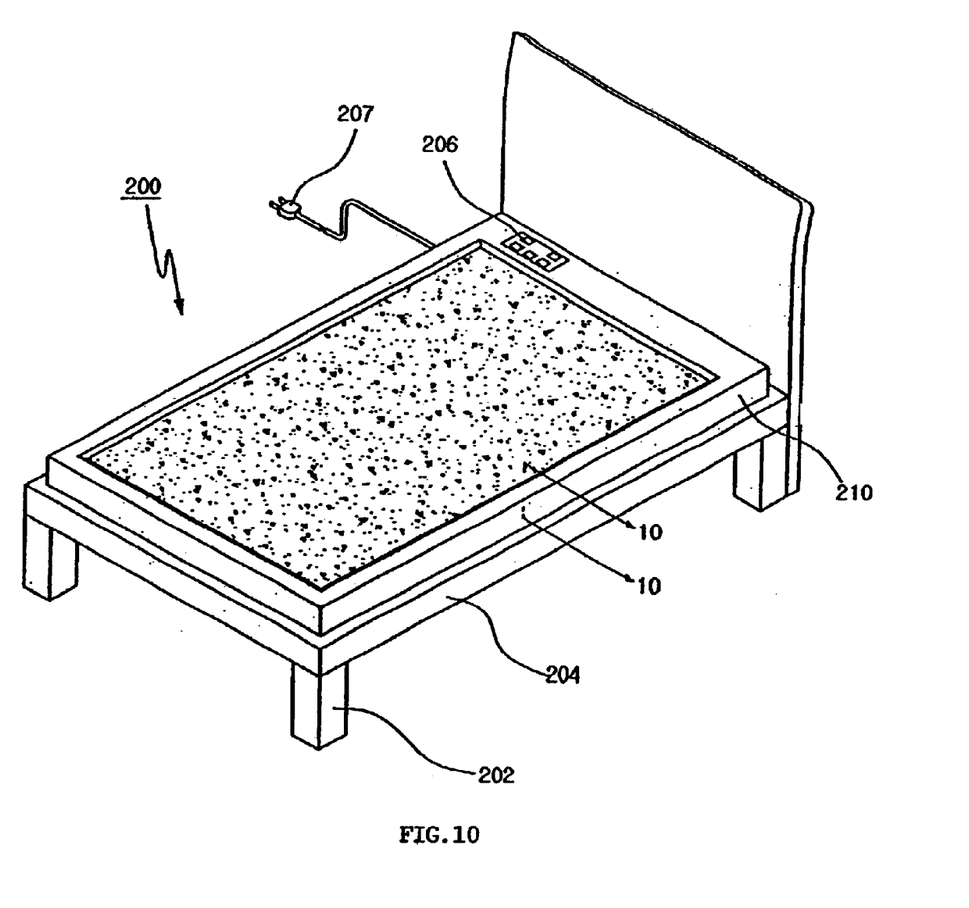
FIG. 10 is a perspective view showing a bed for diagnosis having functions of blocking a water vein and an electromagnetic wave and generating an ultra-long wave according to another embodiment of the present invention.
Figure 11:
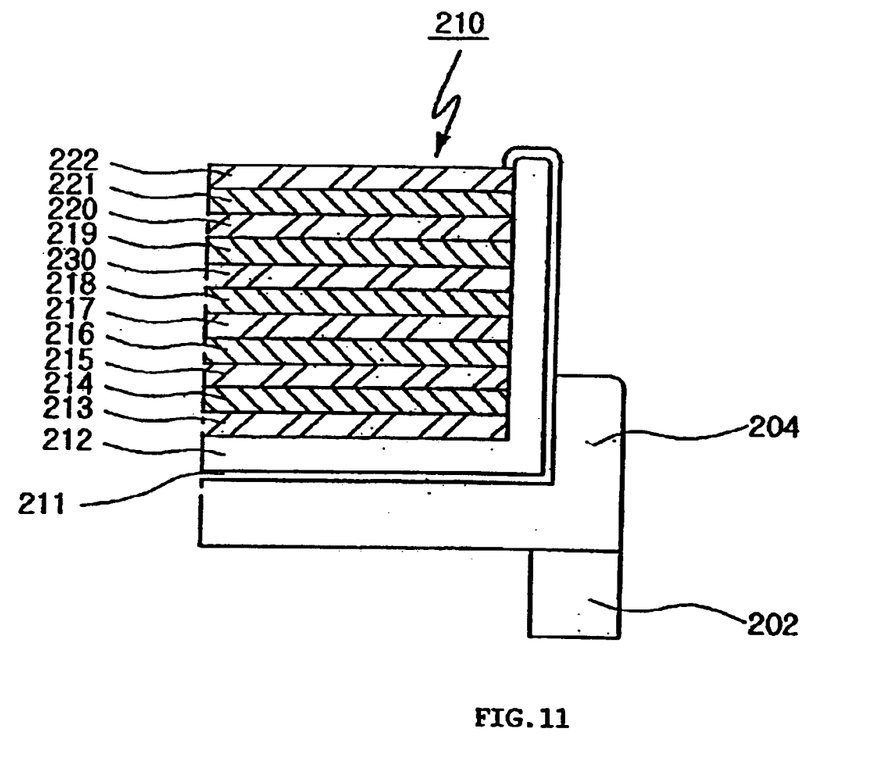
FIG. 11 is an enlarged view taken along line 10—10 of FIG. 10.

FIG. 10 is a perspective view showing a bed for diagnosis having functions of blocking a water vein and an electromagnetic wave and generating an ultra-long wave according to another embodiment of the present invention. FIG. 11 is an enlarged view taken along line 10—10 of FIG. 10.

As shown in FIGS. 10 and 11, the bed 200 comprises a plurality of supporting legs 202, a bedplate 204 mounted on the supporting legs 202, an upper plate 210 mounted over the bedplate 204 and an electromagnetic wave absorbing section (not shown) connected to the upper plate 210 to block electromagnetic waves.

The plurality of supporting legs 202 have the same plane and are fixed to the four corners of the bedplate 204.

The bedplate 204 mounted on the supporting legs 202 has a shape of hexahedron with an open top. The bedplate 204 and the supporting legs 202 can be made of wood, metal or synthetic resin or an equivalent thereof and are not to be limited to a particular material.

The upper plate 210 is mounted over the bedplate 204. The upper plate 210 consists, from the bottom, of an outer cover 211 made of a natural or synthetic leather, an outer frame 212 made of wood to exhibit superior heat insulation, a water vein blocking alumina 213, a dampproof paper 214, urethane 215 with superior heat insulation, an insulating sheet 216 for blocking a leakage current, a calescent carbon heater 217, an insulating sheet 218 for blocking a leakage current, a copper wire 219 for blocking a water vein, a copper plate 220 for blocking a water vein and an electromagnetic wave, a biogene 221 for generating far-infrared rays and a hardened layer 222.

The outer frame 212 is substantially in the shape of a hexahedron with an open top, and is enveloped by the outer cover 211. The other elements of the upper plate 210 are laid in regular sequence within the outer frame 212.

Like the bed 100 according to the first embodiment of the invention, the bed 200 according to the second embodiment includes all the elements for performing functions of generating an ultra-long wave and blocking a water vein and an electromagnetic wave and for producing a thermotherapy effect. Since such elements are the same as those adopted in the bed 100, a detailed explanation thereof will be omitted.

As described above, the bed for diagnosis having functions of blocking a water vein and an electromagnetic wave and generating an ultra-long wave according to the, present invention can prevent the influence of underground water veins by the alumina, copper wire and copper plate included in the upper plate.

Further, the carbon heater offers a thermotherapy effect to a patient laying on the bed to alleviate pains on the body and help effective working of drugs.

The electromagnetic wave absorbing section absorbs and eliminates electromagnetic waves, which may be generated from the carbon heater or the like, so as to prevent the patient from being exposed to the electromagnetic waves.

The ultra-long wave generating section generates ultra-long waves that directly work on the patient laying on the bed, thereby rapidly alleviating pains on the body and providing an environment advantageous to the health.

Also, the bed for diagnosis according to the present invention includes a biogene, as well as a stone layer or an ocher layer as the hardened layer, in order to emit large amounts of far-infrared rays.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A bed for diagnosis having functions of blocking a water vein and an electromagnetic wave and generating an ultra-long wave, said bed comprising:
   a plurality of supporting legs each having a wheel for horizontal movement at the lower end thereof;
   at least one height adjusting plate at the upper part of said supporting legs;
   a metal frame surrounding said height adjusting plate and fixed at the upper part of said supporting legs;
   an upper plate mounted over said height adjusting plate and said metal frame and consisting, from the bottom, of an outer cover, an outer frame, a water vein blocking alumina, a dampproof paper, urethane, an insulating sheet, a calescent carbon heater, an insulating sheet, an ultra-long wave generating section, a copper wire for blocking a water vein, a copper plate for blocking a water vein and an electromagnetic wave, a biogene and a hardened layer; and
   an electromagnetic wave absorbing section connected to said copper plate of said upper plate by a conductive wire for absorbing and eliminating electromagnetic waves.

2. The bed for diagnosis according to claim 1, wherein said hardened layer of said upper plate comprises a stone selected from granite, emerald, yellow jade, corundum, blue elvan and yellow elvan which contain a large amount of germanium.

3. The bed for diagnosis according to claim 1, wherein said hardened layer of said upper plate is an ocher layer formed by mixing 60% by weight of reddish brown clay, 15% by weight of silicon dioxide, 10% by weight of mineral powder (biotite), 7% by weight of a thickener, 3% by weight of pulp and 5% by weight of anhydrite, and extrusion molding the mixture.

4. The bed for diagnosis according to claim 1, wherein a control section for supplying power is provided on the outer frame of said upper plate and said carbon heater is connected to said control section.

5. The bed for diagnosis according to claim 1, wherein one end of said electromagnetic wave absorbing section, which has a resistance R, a condenser C and an inductor L in parallel connection to a power line, is connected by a conductive wire to said copper plate for blocking a water vein and an electromagnetic wave.

6. The bed for diagnosis according to claim 1, wherein said ultra-long wave generating section comprises substantially bar-type permanent magnets and a plurality of ultra-long wave coils winding around the permanent bar magnets, and wherein an alternating current is supplied to said ultra-long wave coils from the control section.

7. The bed for diagnosis according to claim 1, wherein a height adjuster for adjusting the height of the height adjusting plate is provided on the outer periphery of said metal frame to control the height of at least one height adjusting plate, thereby changing the slope of said upper plate.

8. A bed for diagnosis having functions of blocking a water vein and an electromagnetic wave and generating an ultra-long wave, said bed comprising:
a plurality of supporting legs having the same plane;
a bedplate mounted on the supporting legs and having a shape of hexahedron with an open top;
an upper plate mounted over said bedplate and consisting, from the bottom, of an outer cover, an outer frame, a water vein blocking alumina, a dampproof paper, urethane, an insulating sheet, a calescent carbon heater, an insulating sheet, an ultra-long wave generating section, a copper wire for blocking a water vein, a copper plate for blocking a water vein and an electromagnetic wave, a biogene and a hardened layer; and
an electromagnetic wave absorbing section connected to said copper plate of said upper plate by a conductive wire for absorbing and eliminating electromagnetic waves.

* * * * *